United States Patent [19]
Kellenberger et al.

[11] Patent Number: 4,699,823
[45] Date of Patent: Oct. 13, 1987

[54] NON-LAYERED ABSORBENT INSERT HAVING Z-DIRECTIONAL SUPERABSORBENT CONCENTRATION GRADIENT

[75] Inventors: Stanley R. Kellenberger, Appleton; David L. Zenker, Neenah, both of Wis.

[73] Assignee: Kimberly-Clark Corporation, Neenah, Wis.

[21] Appl. No.: 767,950

[22] Filed: Aug. 21, 1985

[51] Int. Cl.⁴ ................................................. B32B 7/02
[52] U.S. Cl. .................................... 428/219; 428/212; 428/218; 428/283; 428/323; 428/913; 604/368; 604/378
[58] Field of Search ................ 604/368, 378; 428/218, 428/219, 281, 283, 323, 402, 913, 212

[56] References Cited

U.S. PATENT DOCUMENTS

| | | | |
|---|---|---|---|
| 1,702,530 | 2/1929 | Williams | 128/290 |
| 3,073,309 | 1/1963 | Mosier | 128/290 |
| 3,121,427 | 2/1964 | Mosier | 128/284 |
| 3,669,103 | 6/1972 | Harper et al. | 128/156 |
| 3,670,731 | 6/1972 | Harmon | 128/284 |
| 3,888,257 | 6/1975 | Cook et al. | 128/296 |
| 3,968,798 | 7/1976 | Hokanson | 128/284 |
| 4,103,062 | 7/1978 | Aberson et al. | 428/283 |
| 4,105,033 | 8/1978 | Chatterjee et al. | 128/285 |
| 4,186,165 | 1/1980 | Aberson et al. | 264/112 |
| 4,226,237 | 10/1980 | Levesque | 128/285 |
| 4,333,462 | 6/1982 | Holtman et al. | 128/287 |
| 4,333,465 | 6/1982 | Wiegner | 128/290 |
| 4,381,782 | 5/1983 | Mazurak et al. | 604/368 |
| 4,381,783 | 5/1983 | Elias | 604/368 |
| 4,410,324 | 10/1983 | Sabee | 604/368 |
| 4,578,068 | 3/1986 | Kramer et al. | 428/219 |

FOREIGN PATENT DOCUMENTS 1406615 9/1975 United Kingdom .
2145661 4/1985 United Kingdom .

Primary Examiner—James J. Bell
Attorney, Agent, or Firm—Paul Yee

[57] ABSTRACT

An improved absorbent article includes a layer of absorbent material which has a length, a width and a thickness. Particles of superabsorbent material are distributed within the absorbent material layer, and these superabsorbent particles are disposed to form a substantially continuous, non-step-wise, positive concentration gradient of superabsorbent through at least a portion of the thickness of the absorbent layer.

18 Claims, 11 Drawing Figures

NON-LAYERED ABSORBENT INSERT HAVING Z-DIRECTIONAL SUPERABSORBENT CONCENTRATION GRADIENT

DESCRIPTION

1. Field of the Invention

The present invention is related to absorbent articles. More particularly, the present invention is related to absorbent articles which contain particles of superabsorbent materials dispersed therein.

2. Background of the Invention

Disposable articles, such as diapers, sanitary napkins, incontinence garments, bandages and the like, employ pads or batts of absorbent material to absorb and retain liquids, such as body exudates. Significant effort has been devoted to increasing the amounts of liquids that can be retained by the absorbent pads. By increasing the absorbent capacity of the pads, the physical dimensions, such as the thickness, of the pads can advantageously be reduced.

Various types of absorbent pads have incorporated superabsorbent materials, such as superabsorbent polymers, to increase the liquid retention capacity of the pads. In certain configurations, the superabsorbent materials have been selectively located in particular discrete areas of the pad. For example, U.S. Pat. No. 3,888,257 issued June 10, 1975 to R. Cook, et al. describes a disposable absorbent article which includes a matrix of fiberized wood pulp. Hydrocolloid polymer particles are located in a three-dimensional dispersion in a central zone or strip of the fiberized matrix. U.S. Pat. No. 4,333,462 issued June 8, 1982 to D. Holtman et al. describes an absorbent structure which includes an absorbent batt, containing two reservoirs. The first reservoir opens toward the cover of the article, and the second reservoir is located below the first reservoir and contains particles of superabsorbent. U.S. Pat. No. 4,381,783 issued May 3, 1983 to R. Elias describes an absorbent article which includes an absorbent layer having at least one discrete internal pocket. The pocket contains a uniform admixture of discrete superabsorbent particles and discrete introfying particles. U.S. Pat. No. 4,381,782 issued May 3, 1983 to P. Mazurak, et al. discloses highly absorbent, low density fibrous structures, such as webs or batts which include mixtures of powdered or microcrystalline hydrogel preparations with surfactant treated filler materials. The hydrogel preparations are located in a transverse band or strip extending across the width of the absorbent batt. U.S. Pat. No. 4,333,465 issued June 8, 1982 to G. Wiegner discloses a sanitary towel which includes an absorptive hydrophilic fiber filling material. An internal core of the filling material has an insert which contains, highly absorptive polymers therein. British Pat. No. 1,406,615 published Sept. 17, 1975 describes absorbent pads which include absorptive gelling agents, such as cellulose ethers, cellulose esters, and acetyl starch. The gelling agent is impregnated into selected central areas of the pad.

The following patents disclose absorbent pads which include centralized layers or zones composed of material which are more absorbent than the other portions of the pad: U.S Pat. No. 1,702,530 issued Feb. 19, 1929 to H. Williams; U.S. Pat. No. 3,073,309 issued Jan. 15, 1963 to J. E. J. Mosier; and U.S. Pat. No. 3,121,427 issued Feb. 18, 1964 to J. M. Mosier.

U.S. Pat. No. 3,669,103 issued June 13, 1972 to B. Harper, et al. discloses absorbent articles comprised of body-conforming supports which contain dry, solid, water-swellable, water-insoluble polymeric sorbents composed of lightly cross-linked polymers. U.S. Pat. No. 3,670,731 issued June 20, 1972 to C. Harmon discloses an absorbent dressing which includes a water soluble hydrocolloidal composition. The hydrocolloid can be intermixed with the fibers of an absorbent pad, or may be located in a discrete layer along a major surface of the absorbent article.

Absorbent pads have included superabsorbent particles disposed in strip-type patterns. For example, U.S. Pat. No. 3,968,798 issued July 13, 1976 to K. Hokanson describes an absorbent pad in a C-fold configuration which has a middle portion thereof loaded with a uniform dispersion of hydrocolloid polymer particles. U.S. Pat. No. 4,410,324 describes a disposable diaper which has an absorbent pad folded intermediate the ends to provide increased absorbent material in the crotch region. Hydrocolloidal material can be located in strips along marginal portions of the absorbent pad.

U.K. Patent Application No. GB 2 145 661A describes an absorbent article comprised of at least two discrete super absorbent layers and a wicking means. The wicking means extends about and between the superabsorbent layers to help distribute liquid.

Conventional absorbent articles, such as those described above, have not been able to efficiently utilize the full potential of the superabsorbent materials. When the superabsorbent materials absorb liquid, they typically swell and form a gel structure. This gel structure often blocks the further transfer of liquid into the remaining absorbent structure. As a result, the liquid may be unable to reach the remaining super absorbent material and the efficiency of the absorbent article decreases significantly. Attempts to overcome this "gel blocking" phenomenon have included various techniques. For example, the technique of uniformly dispensing the superabsorbent particles within a pad of absorbent and the technique of employing discrete wicking mechanisms to distribute the liquid throughout the quantity of superabsorbent have been employed. However, conventional techniques to reliably distribute the liquid and fully utilize the total amount of superabsorbent material have not been completely satisfactory.

A further shortcoming exhibited by conventional absorbent structures employing superabsorbents has been an undesirable, slippery and gel-like feeling produced on the surfaces of the absorbent structure. This slimy feeling has been particularly objectionable in absorbent pads incorporated into garments such as infant diapers, incontinence garments and feminine napkins. Conventional absorbent articles have addressed this problem by selectively isolating the superabsorbent material at locations away from those surfaces of the article that contact the body of a wearer. For example, the superabsorbent material has been restricted to a central core region of the structure and has been restricted to an outside layer of the structure away from the body of the wearer. These techniques, however, have been susceptible to the gel-blocking problem. As a result, conventional absorbent structures have not adequately isolated the superabsorbent produced gel away from the body surfaces of the garment wearer while also adequately reducing gel blocking.

BRIEF DESCRIPTION OF THE INVENTION

The present invention provides an improved absorbent article which includes a layer of absorbent material having a length, a width, and a thickness. Particles of superabsorbent material are distributed within the absorbent material layer, and these superabsorbent particles are disposed to form a substantially continuous, non-step-wise and non-layered concentration gradient of superabsorbent material through at least a portion of the thickness dimension of the absorbent layer.

The distinctive arrangement of the superabsorbent in a concentration gradient through the thickness of the absorbent layer reduces the occurrence of gel blocking and improves the reliability of the distribution of liquid throughout the quantity of superabsorbent material. In addition, the location of increased concentrations of superabsorbent in selected regions of the absorbent layer reduces the potential contact of gel material with the body of the garment wearer. As a result, the article of the invention provides an absorbent structure which more efficiently utilizes a given quantity of superabsorbent material and improves the comfort of the garment.

BRIEF DESCRIPTION OF THE DRAWINGS

The invention will be more fully understood and further advantages will become apparent when reference is made to the following detailed description of the invention and the drawings in which.

DETAILED DESCRIPTION OF THE INVENTION

While the following detailed description is made in the context of a disposable diaper, it is readily apparent that the absorbent structure of the present invention can also be employed in various other types of articles, such as sanitary napkins, incontinence garments, bandages, absorbent wipes, and the like. All of such articles are contemplated as being within the scope of the present invention.

Figure 1:
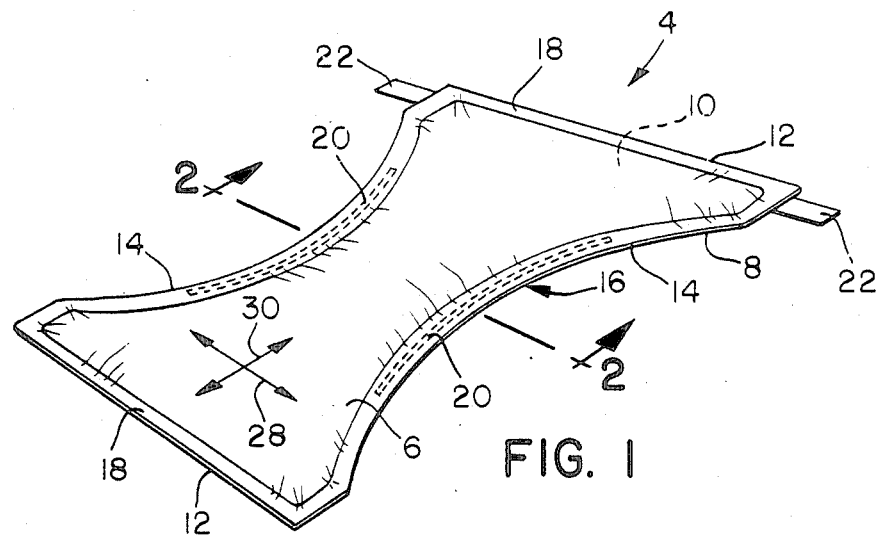
FIG. 1 representatively shows a perspective view of a disposable garment constructed in accordance with the present invention.

Referring to FIG. 1, a disposable diaper 4 includes a liquid-permeable inner liner 6, a liquid-impermeable outer layer, such as backsheet 8, and an absorbent layer, such as batt 10, with the batt located between the liner and the backsheet. The inner liner and the backsheet are larger than the absorbent batt, and have end marginal portions 12 extending beyond the ends of batt 10. The liner and backsheet also have side marginal portions 14 extending beyond the sides of the batt. Typically, liner 6 and backsheet 8 are secured to each other along the marginal portions 12 and 14.

Conventional materials are employed for the component elements of diaper 4. Liner 6 may be any soft, flexible porous sheet which passes fluids therethrough, and may, for example, be comprised of a nonwoven web or sheet of polyolefin fibers, such as polypropylene fibers. The liner may also be comprised of wet strength tissue paper, a spunwoven filament sheet, or the like. In addition, the liner may be treated with a surfactant to aid in liquid transfer.

Backsheet 8 is a liquid-impermeable layer, and may be comprised of a thin web or sheet of plastic film, such as polyethylene, polypropylene, polyvinyl chloride or the like. The backsheet may be transparent or may have an embossed or matt surface to render it opaque.

Absorbent batt 10 may be of any suitable material, and is generally a cellulosic material, such as an airformed batt of wood pulp fibers commonly known as "fluff". Absorbent, creped wadding or tissue sheets 9 and 11 can be located between absorbent batt 10 and liner 6 and backsheet 8, respectively.

Liner 6, backsheet 8, and absorbent batt 10 may be combined with one another in any suitable manner to form the finished diaper. The elements may be bonded to one another by strips or patterns of hot melt or pressure sensitive adhesive, overall or patterned heat sealing, strips of double faced, pressure sensitive adhesive tape, or the like. A particularly effective bonding system employs spaced, parallel lines of hot melt adhesive placed on the interior surface of backsheet 8. The absorbent batt is bonded to the backsheet along portions of the adhesive lines, and liner 6 is bonded to backsheet 8 along other portions of the adhesive lines that are located within the marginal portions 12 and 14 but outside the region of batt 10.

Diaper 4 has a generally hourglass or I-shape, which includes a narrowed crotch section 16 near the center of the diaper and includes waistband sections 18 at each end of the diaper. Elongate elastic means 20 are secured in place adjacent absorbent batt 10 and on each side thereof to develop gathered elastic leg portions that are conformable with an infant's legs. Conventional pressure sensitive tapes 22 are attached to one waistband section 18. Diaper 4 is fitted to an infant with inner liner 6 against the infant's skin. One waistband portion encircles part of the infant's waist and the other waistband portion encircles the balance of the infant's waist. The two waistband portions are overlapped and joined together by pressure sensitive adhesive tapes 22 which operate to hold the diaper in place.

Figure 2:
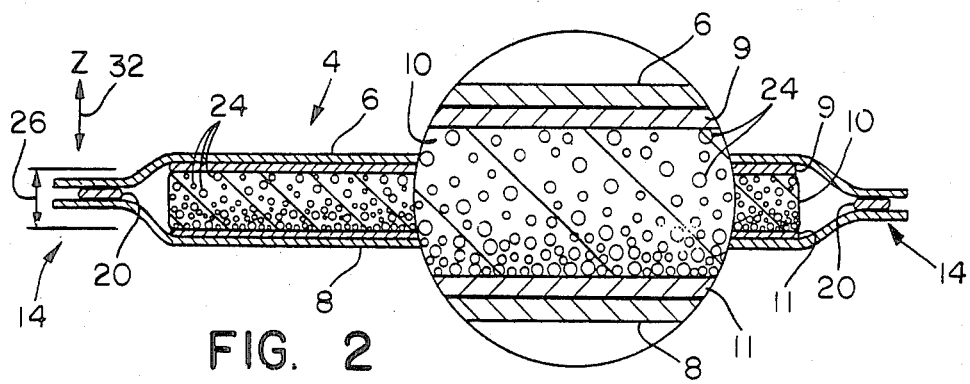
FIG. 2 is a cross-sectional, elevational side view of the disposable garment taken along section 2—2 of FIG. 1, and representatively showing a superabsorbent concentration gradient comprised of randomly-sized superabsorbent particles.

As illustrated in FIGS. 1 and 2, diaper 4, in general, and absorbent batt 10, in particular, have a longitudinal length dimension 30 and a lateral, transverse width dimension 28. In addition, batt 10 has a thickness dimension 26 which extends substantially in the z-direction 32. As illustrated in FIG. 2, particles of superabsorbent material 24 are distributed within the layer of absorbent material which comprises batt 10. The superabsorbent particles are disposed to form a substantially continuous, non-step-wise concentration gradient of superabsorbent through the thickness dimension of the absorbent layer. As a result, the superabsorbent particles are disposed in a substantially non-layered configuration. The superabsorbent is not restricted to a particular level or layer within the thickness of the absorbent batt.

For the purposes of the present invention, the term "superabsorbent" refers to materials which are capable of absorbing and retaining at least about 15 times their own weight in body fluids under a 0.5 psi pressure. Such superabsorbent materials include gums, such as guar. Superabsorbents also include polymers such as sodium polypropenoic acid, starch-grafted polypropenoic acid, polypropenoic acid amide, and the like.

Figure 3:
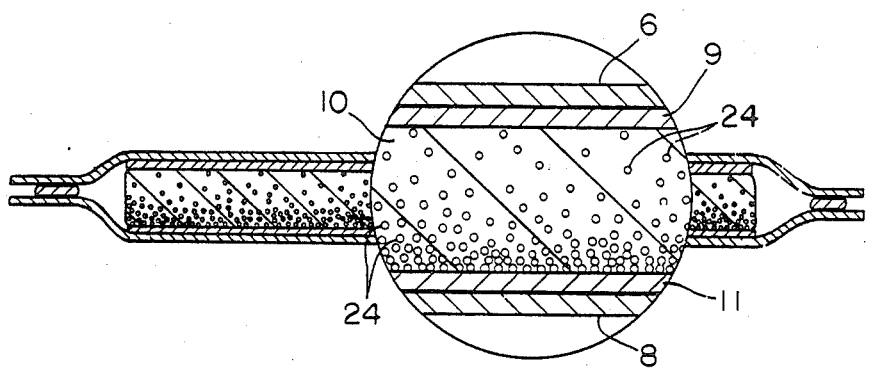
FIG. 3 representatively shows a superabsorbent concentration gradient comprised of substantially uniformly-sized superabsorbent particles.
Figure 4:
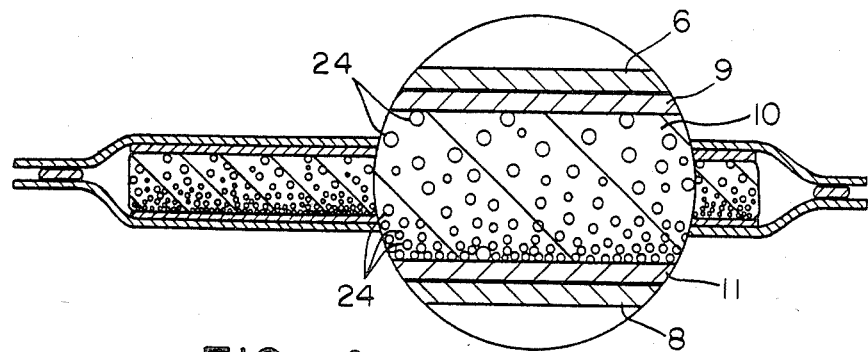
FIG. 4 representatively shows a superabsorbent concentration gradient in which larger-sized particles are predominantly located near the body side of the absorbent batt.

Referring to FIG. 3, absorbent batt 10 has two major surfaces. One major surface is located in proximate relation with liner 6, and is commonly referred to as the bodyside of the batt. The other major surface of batt 10 is located in proximate relation to backsheet 8 and is commonly referred to as the outer side of batt 10.

To improve the absorbency of batt 10, the superabsorbent particles 24 are distributed to form a concentration gradient as one observes successive levels within the thickness of diaper 4 moving along the z-direction. In the embodiment shown in FIG. 2, the superabsorbent concentration gradually increases over at least a portion of the thickness dimension of diaper 4 to provide a positive gradient as one observes successive levels in a sequence beginning at the bodyside of batt 10 and ending at the outer side of the batt. The superabsorbent particles are substantially uniformly distributed across the width of the absorbent layer, as measured at a particular thickness level in the absorbent batt. The superabsorbent particles are also substantially uniformly distributed along the length of the absorbent layer, as measured at a particular thickness level in the absorbent batt.

In a particular aspect of the invention, the superabsorbent concentration on the bodyside of the batt is less than the average superabsorbent concentration in the batt, and the superabsorbent concentration on the outer side of the batt is greater than the average superabsorbent concentration. For example, the superabsorbent concentration gradually increases as one observes the concentration at various levels in the batt taken as one moves from the bodyside surface to the outer surface.

For the purposes of the present invention, localized superabsorbent concentrations are determined by taking a slice through the absorbent batt along a plane which is generally perpendicular to the z-direction to expose a selected layer within batt 10. The percentage of the exposed area of the batt covered by superabsorbent particles is considered to be the percent areal concentrations. Once the areal percent concentration is determined, the weight percent concentration can be calculated by assuming a spherical particle shape, raising the percent areal concentration to the 3/2 power, and by taking into account the densities of the different materials within the slice. The average superabsorbent areal concentration within batt 10 is determined by exposing at least three layers within the batt to determine the local areal concentrations thereof and then calculating the average of these areal concentrations. The average weight concentration can be calculated in a similar fashion, taking into account the different densities of the superabsorbent and regular-absorbent materials.

The illustrated absorbent structure provides several significant advantages. The lower concentration of superabsorbent particles near the bodyside surface of batt 10 and the higher concentration of particles near the outer surface of the batt advantageously reduce the migration of superabsorbent during use. In addition, the concentration gradient of superabsorbent particles can improve absorbency performance. The lower concentration of a superabsorbent at the bodyside surface of the batt reduces gel blocking at the bodyside surface. As a result, liquid run-off and leakage are reduced, and there is a more complete utilization of the entire absorbent structure. The lower superabsorbent concentration at the bodyside surface of batt 10 can also act as a reservoir which can hold a sudden input of fluid and then release it at a relatively lower rate to the regions of the batt having higher concentrations of superabsorbent.

In the embodiment illustrated in FIG. 2, the superabsorbent particle size within the concentration gradient is essentially random. The particle size distribution, however, may have other configurations. For example, as illustrated in FIG. 3, the superabsorbent concentration gradient may be comprised of particles which have a substantially uniform size.

In another aspect of the invention, the superabsorbent particles located near the bodyside of batt 10 are on the average, larger in dimension than the superabsorbent particles located toward the outer side of the batt. In particular, superabsorbent particles located near the bodyside of batt 10 range from about 300–1,000 micrometers in average diameter. The superabsorbent particles located toward the outer side of batt 10 are less than about 300 micrometers in average diameter. At levels between the bodyside and outer side of batt 10, the average particle size generally decreases as one observes the sizes moving from the bodyside of batt 10 toward the outer side of the batt.

Figure 7:
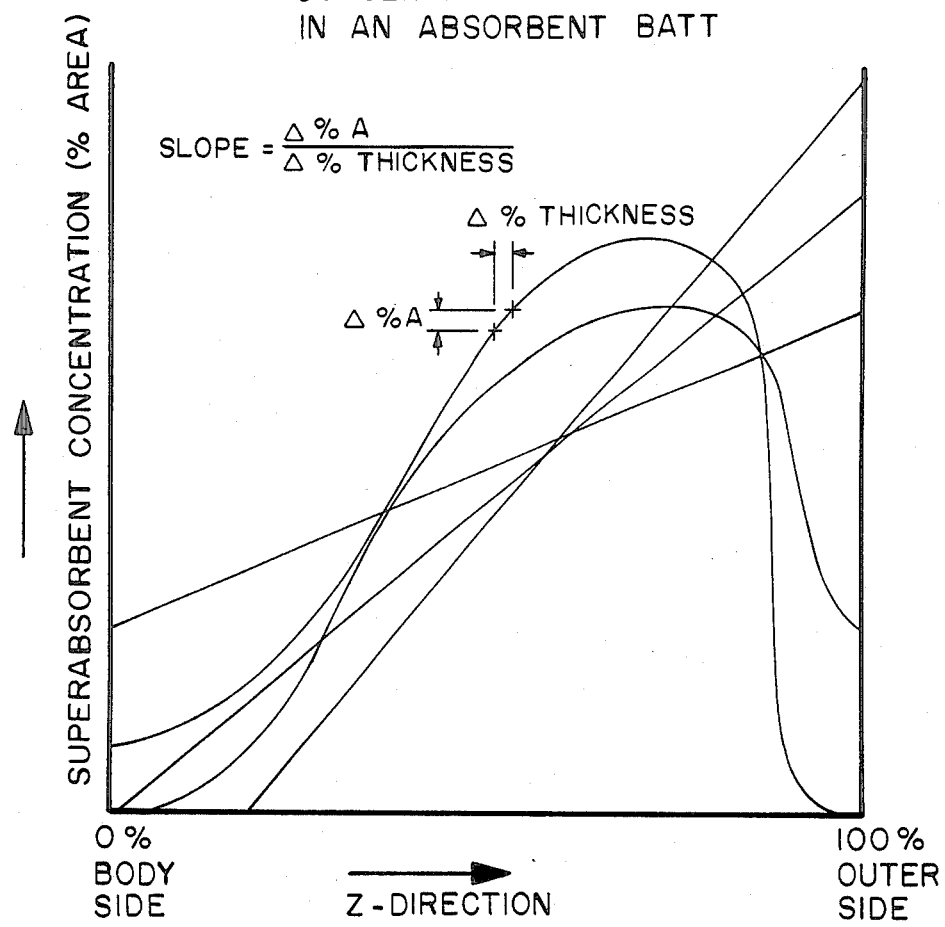
FIG. 7 shows a graph which illustrates examples of approximate concentration gradients through the thickness dimension of the absorbent article of the invention.
Figure 11:
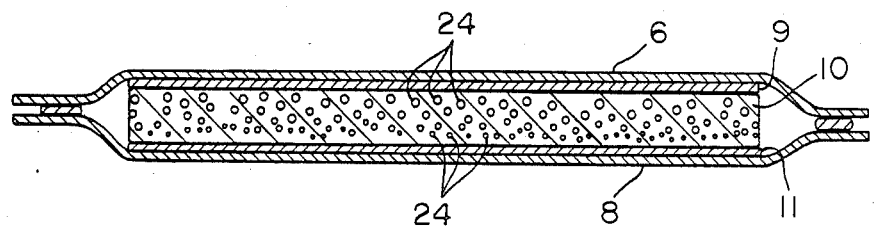
FIG. 11 representatively shows a superabsorbent concentration gradient which begins at a discrete distance away from the bodyside of the absorbent layer and ends at a discrete distance away from the outer side of the absorbent layer.
Figure 10:
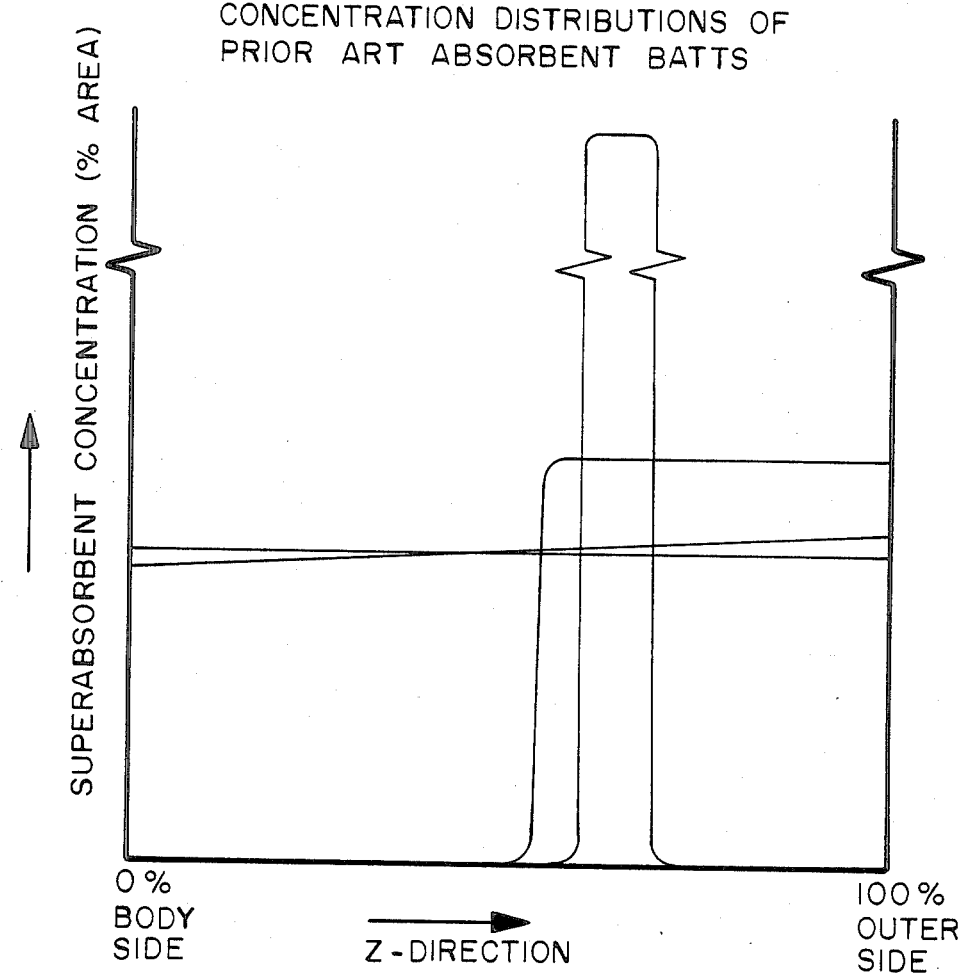
FIG. 10 shows a graph which illustrates the distribution of superabsorbent particles in prior art garments having a substantially uniform dispersion of superabsorbent particles in an absorbent batt, or having the particles substantially restricted to discrete layered zones.

In still another particular aspect of the invention, the concentration of superabsorbent is approximately zero for a discrete distance into batt 10, as measured from the bodyside of the batt. As a result, the z-directional superabsorbent concentration gradient rises from zero beginning at a point below the top, bodyside of batt 10, as illustrated in FIGS. 7 and 11. The superabsorbent concentration over a discrete distance into batt 10, as measured from the outer side of the batt, can also be zero. As a result, the z-directional superabsorbent concentration gradient ends or returns to zero before reaching the outer surface of batt 10.

For the purposes of the present invention, the positive z-directional concentration gradient is considered to begin at that point proximate to the bodyside of batt 10 at which the superabsorbent concentration has a substantially non-zero value and begins a gradual increase as one observes successive layers within the batt further from the batt bodyside. Similarly, the z-directional superabsorbent concentration is considered to end at the outer surface of the batt, or at that point proximate to the outer surface of batt 10 at which the concentration falls to a substantially zero value.

In particularly effective aspects of the invention, the ratio of the superabsorbent concentration at the beginning of the gradient to the superabsorbent concentration at the end of the gradient is at least 1:2 as determined by areal percent concentrations, or at least about 1:3 as determined by percent weight concentrations. For improved effectiveness, the beginning to end gradient ratio is at least about 1:5 as determined by areal percent, or at least about 1.11 as determined by weight percent. More preferably, the beginning-to-end concentration gradient ratio is at least about 1:10 as determined by areal percent, or at least about 1.30 as determined by weight percent.

In other preferred aspects of the invention, the concentration gradient line has a positive slope within the range of about 0.02–0.5, preferably has a positive slope within the range of 0.03–0.4, and more preferably has a positive slope within range of about 0.05–0.2. The slope of the concentration gradient line is determined by taking the z-directional change (delta) in the percent areal superabsorbent concentration and dividing it by the change (delta) in the percent of the z-directional thickness of batt 10 over which the change in percent areal concentration occurs. This determination is illustrated in FIG. 7.

The relative percent concentrations are determined by splitting batt 10 along a plane which is substantially perpendicular to the z-direction. This exposes a selected surface level within the batt. The relative areal concentration is then determined by comparing the amount of area covered by superabsorbent particles relative to the total exposed area of the batt. The weight percent concentrations can then be calculated employing the density of the absorbent fluff material and the density of the superabsorbent particles.

The percent of the area of a particular level within batt 10 that was covered by superabsorbent particles was determined employing the following procedure. A selected level was exposed by cutting, peeling, or otherwise removing overlying batt material. The exposed level was then misted with an indicator solution to color, and to optionally expand, the superabsorbent particles. The indicator solution created a contrast between the superabsorbent particles and the batt material, and the contrasting areas were measured with image analysis equipment, such as a Cambridge Quantimet 900 Image Analysis system to determine the relative percent area covered by superabsorbent particles.

In an example of the above procedure, the superabsorbent particles contained starch and were misted with an aqueous solution of potassium iodide ($KI_2$). The aqueous solution was prepared from a stock composed of 10 grams KI, 1 gram $I_2$ and sufficient water to provide a total liquid solution volume of 100 ml. The actual misting solution contained 5–10 percent of the stock. A gas chromatograph atomizer was positioned 10–12 inches from the batt sample, and the sample was misted for about 5–10 seconds until nucleated, 1–2 mm. diameter droplets around the sample. The aqueous $KI_2$ indicator solution expanded the superabsorbent particles and multiplied their area of coverage by a factor of about 2. This swelling and expansion of the superabsorbent particles increased the sensitivity of the test. Appropriate adjustments were made to the final image analysis readings to compensate for the particle expansion and to determine the area covered by dry particles.

Figure 5:
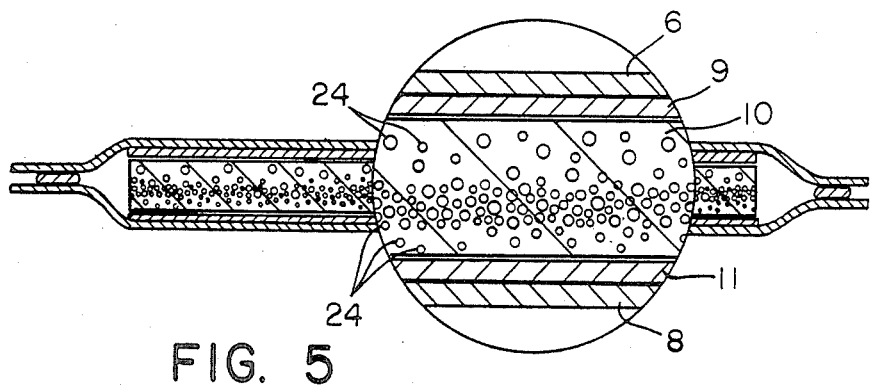
FIG. 5 representatively shows a superabsorbent concentration gradient in which the concentration reaches a maximum in a central portion of the absorbent batt.

FIG. 5 illustrates an aspect of the invention in which the superabsorbent concentration at a central core of batt 10 is greater than at either the bodyside or outer side surfaces of the batt. For improved performance, the areal percent superabsorbent concentration at the center of the concentration profile gradient is approximately 10 times the superabsorbent concentration at the ends of the gradient profile.

Figure 6:
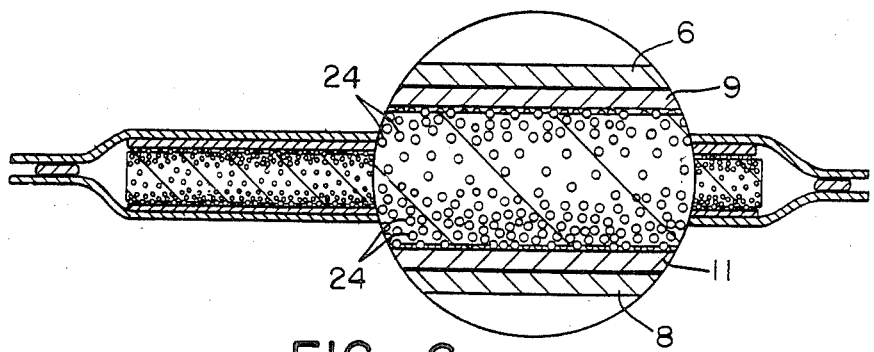
FIG. 6 representatively shows a superabsorbent concentration gradient in which the concentration has a minimum located between the body side and outer side of the absorbent batt.
Figure 8:
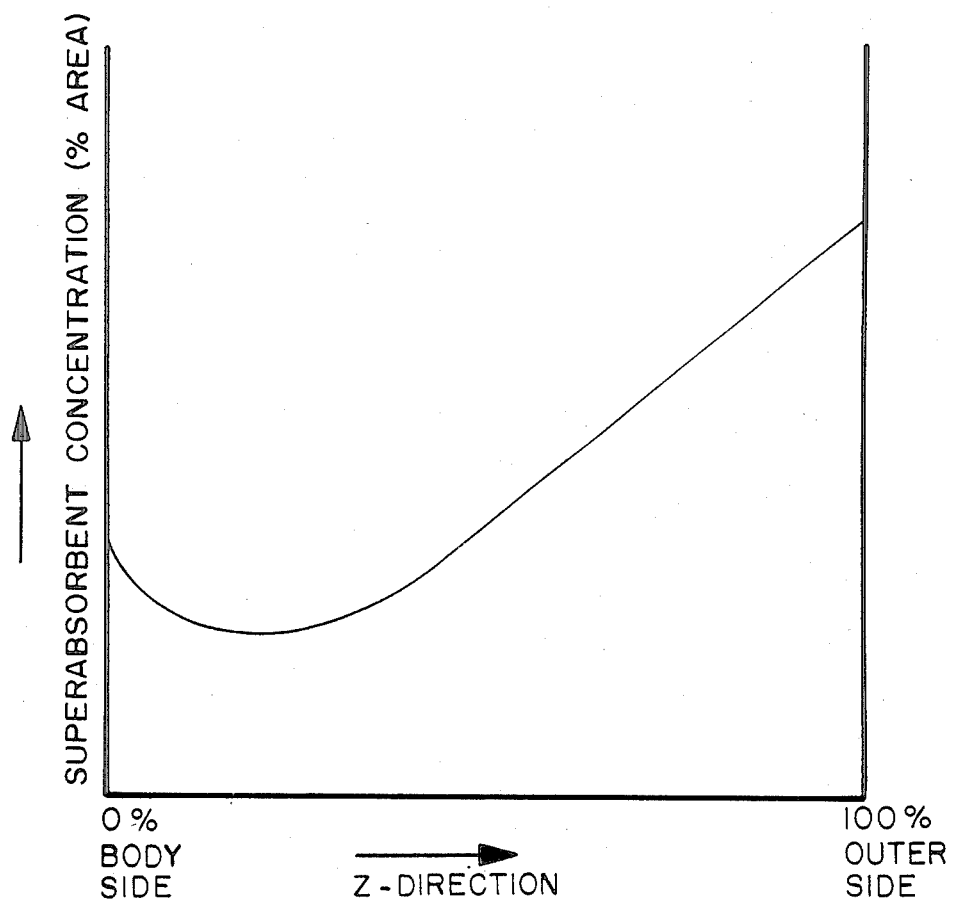
FIG. 8 shows a graph which illustrates a superabsorbent concentration gradient in which the concentration reaches a minimum at a location between the body side and outer side of the absorbent batt.
Figure 9:
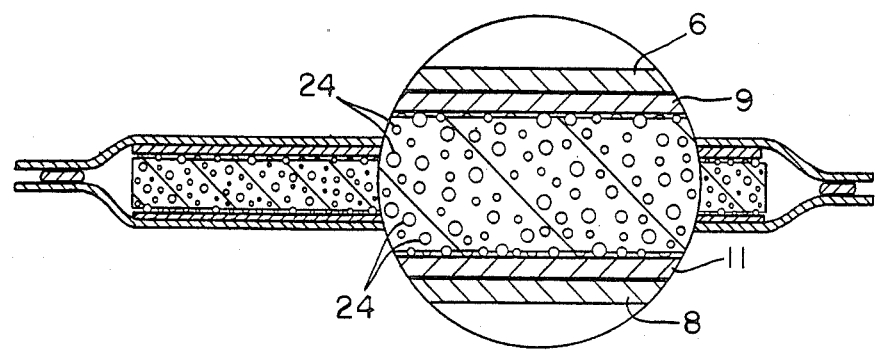
FIG. 9 is a cross-sectional, elevational side view of a prior art disposable garment which has a substantially uniform dispersion of superabsorbent particles in an absorbent batt.

FIGS. 6 and 8 illustrate an aspect of the invention in which the superabsorbent concentration at a center region of batt 10 is less than the concentration at either the bodyside or outer side of the batt. In the shown embodiment, the superabsorbent areal percent concentration decreases as one observes the areal concentration at successive levels within batt 10 beginning from the body side of the batt. The areal percent concentration reaches a minimum and then begins to increase to provide a positive slope to the concentration gradient. Also, the superabsorbent concentration on the bodyside of the batt is less than the superabsorbent concentration on the outer side of the batt.

For improved performance, the total quantity of superabsorbent particles comprises 12–15 weight percent of the composite absorbent batt. The composite batt includes both the conventional absorbent material and the superabsorbent material. When the conventional fiberous absorbent material is composed of wood pulp fluff, the fluff is densified through compression to produce a fluff density within the range of about 0.13–0.18 grams per cc. Quantities of superabsorbent greater than about 15 weight percent do not improve and may actually reduce absorbent performance. Fluff densities lower than about 0.13 grams per cc. produce poor fluid distribution, while fluff densities greater than about 0.18 grams per cc. do not further improve fluid distribution and can produce undesirable attributes, such as hard spots, stiffness, poor fluid intake and poor fit.

The following examples are provided to give a more detailed understanding of the invention. The specific materials, quantities, and other parameters stated therein are exemplary and are not intended to specifically limit the scope of the invention.

EXAMPLES

Sample diaper articles were constructed in accordance with the present invention, and had the characteristics set forth in Table 1.

TABLE 1

SUPERABSORBENT Z-DIRECTIONAL DISTRIBUTION

| SAMPLE | DESCRIPTION | % AREA COVERED BY SAM | | | CONCENTRATION RATIO:BODYSIDE TO OUTER SIDE | | SLOPE (CHNG % AREA/ CHNG % DEPTH) |
|---|---|---|---|---|---|---|---|
| | | BODYSIDE | CENTER | OUTER SIDE | % AREA | % WEIGHT* | |
| 1 | Absorbent batt with 12% (by weight) SANWET IM1000 in fluff | 0.21 | 2.85 | 5.6 | 1:27 | 1:139 | +0.54 |
| 2 | Absorbent batt with 12% (by weight) SANWET IM1000 in fluff | 4.25 | 0.6 | 6.2 | 1:1.5 | 1:1.8 | −0.07 (BODYSIDE-CTR) +0.11 (CTR-OUTER SIDE) |

*Approximation by calculation.
SAM = Superabsorbent material

Sample 1 was preferred because it had a positive superabsorbent concentration gradient through the thickness of the batt. Sample 2 was less desirable because of the relatively high superabsorbent concentration near the bodyside of the batt. The desirable positive slope to the concentration gradient did not begin until somewhere in the center portion of the batt.

In contrast to the diapers constructed in accordance of the present invention, a conventional diaper had the characteristics set forth in Table 2.

The conventional diaper had superabsorbent particles dispersed substantially uniformly through the absorbent batt.

TABLE 2

| SAMPLE | DESCRIPTION | % AREA COVERED BY SAM | | | RATIO:BODYSIDE TO OUTER SIDE | | SLOPE (CHNG % AREA/ CHNG % DEPTH) |
|---|---|---|---|---|---|---|---|
| | | BODYSIDE | CENTER | OUTER SIDE | % AREA | % WEIGHT* | |
| 3 | Absorbent batt 12% (by weight) SANWET IM1000 in fluff | 2.2 | 3.05 | 3.9 | 1:1.8 | 1:2.4 | +0.017 |

*Approximation by calculation.
SAM = Superabsorbent material

Some comparative leakage testing data are shown in Table 3. These data indicate that absorbent structures having a lower superabsorbent concentration near the bodyside surface of the batt in combination with a higher superabsorbent concentration near the outer surface of the batt exhibit less leakage of urine and less superabsorbent migration onto the inner liner of the diaper when compared to absorbent structures having a conventional, uniform dispersion of superabsorbent through the absorbent fluff layer.

TABLE 3

PERFORMANCE VS. SUPERABSORBENT Z-DIRECTIONAL DISTRIBUTION

| OVERNIGHT TEST PRODUCT | BODYSIDE/OUTER SIDE SAM DIST. RATIO (AREA) | % URINE ONLY DIAPERS W/SAM ON BSL | LKG 50(b) |
|---|---|---|---|
| 4 g SANWET IM1000/ 30 g fluff | 1:27 | 21% | 250 g |
| 4 g SANWET IM1000/ 30 g fluff | 1:1.5 | 40% | 195 g |
| 4 g DOW DRYTECH SAM 30 g fluff | 1:27(a) | 8% | 247 g |
| 4 g DOW DRYTECH SAM 30 g fluff | 1:1.5(a) | 19% | 223 g |

(a) Distribution ratio based on qualitative analysis.
(b) An LKG 50 value of 250 grams means that 50% of the tested diapers failed before absorbing 250 grams of liquid during overnight use.
SAM = Superabsorbent material
BSL = Bodyside liner

Having thus described the invention in rather full detail, it will be readily apparent that various changes and modifications can be made, all of which are contemplated as being within the scope of the invention as defined by the subjoined claims.

We claim:

1. An absorbent article, comprising:
    (a) a layer of absorbent material having a length, a width and a thickness; and
    (b) particles of superabsorbent material distributed within said absorbent material layer;
    (c) wherein said superabsorbent particles are disposed to form a substantially continuous, non-step-wise positive concentration gradient of superabsorbent through at least a portion of the thickness of said absorbent layer, and wherein said superabsorbent concentration are measured on a weight percent basis.

2. An article as recited in claim 1, wherein said superabsorbent particles are substantially uniformly distributed across the width of said absorbent layer, as measured at a particular thickness level in the absorbent layer.

3. An article as recited in claim 1, wherein said superabsorbent particles are substantially uniformly distributed along the length of said absorbent layer, as measured at a particular thickness level in the absorbent layer.

4. An absorbent article as recited in claim 1, wherein the superabsorbent concentration gradient gradually increases as the superabsorbent concentration is measured at increasing distances away from a bodyside surface of said absorbent layer.

5. An absorbent article as recited in claim 1, wherein the superabsorbent concentration at a bodyside surface of said absorbent layer is less than the average superabsorbent concentration of said absorbent layer, and the superabsorbent concentration at a outer surface of said absorbent layer is greater than said average superabsorbent concentration.

6. An absorbent article as recited in one of claims 1-5, wherein the superabsorbent particles located at the bodyside surface of said absorbent layer are on the average larger than the superabsorbent particles located at the outer surface of said absorbent layer.

7. An absorbent article as recited in claim 1, wherein the superabsorbent concentration is substantially zero for a discrete distance measured into said absorbent layer from the bodyside surface thereof.

8. An absorbent article as recited in claim 1, wherein the superabsorbent concentration is substantially zero for a discrete distance measured into said absorbent layer from the outer surface thereof.

9. An absorbent article as recited in claim 1, wherein the superabsorbent concentration is greater at locations partially through the thickness of said absorbent layer than at the bodyside and outer surfaces thereof.

10. An absorbent article as recited in claim 1, wherein a line representing said superabsorbent concentration gradient has a positive slope within the range of about 0.02–0.5.

11. An absorbent article as recited in claim 10, wherein said concentration gradient line has a positive slope within the range of about 0.03–0.4.

12. An absorbent article as recited in claim 11, wherein said concentration gradient line has a positive slope within the range of about 0.05–0.2.

13. An absorbent article as recited in claim 1, wherein a ratio of the superabsorbent concentration at the beginning of said gradient to the superabsorbent concentration at the end of said gradient is at least about 1:3, as determined by weight percent concentrations.

14. An absorbent article as recited in claim 13, wherein said ratio of superabsorbent concentrations is at least about 1:11, as determined by weight percent concentrations.

15. An absorbent article as recited in claim 14, wherein said ratio of superabsorbent concentrations is at least about 1:30, as determined by weight percent concentrations.

16. An absorbent article as recited in one of claims 7-9 and 10-15, wherein the superabsorbent particles located near the bodyside surface of said absorbent layer are on the average larger than the superabsorbent particles located near the outer surface of said absorbent layer.

17. An abosrbent article as recited in claim 16, wherein the superabsorbent particles near the bodyside surface of said absorbent layer range from about 300–1,000 micrometers in size.

18. An absorbent article as recited in claim 16, wherein the superabsorbent particles located at the outer surface of said absorbent layer are less than about 300 micrometers in size.

* * * * *